United States Patent
Wang

(10) Patent No.: US 7,942,036 B2
(45) Date of Patent: *May 17, 2011

(54) RHEOMETER ALLOWING DIRECT VISUALIZATION OF CONTINUOUS SIMPLE SHEAR IN NON-NEWTONIAN FLUID

(75) Inventor: Shi-Qing Wang, Streetsboro, OH (US)

(73) Assignee: The University of Akron, Akron, OH (US)

(*) Notice: Subject to any disclaimer, the term of this patent is extended or adjusted under 35 U.S.C. 154(b) by 789 days.

This patent is subject to a terminal disclaimer.

(21) Appl. No.: 11/891,455

(22) Filed: Aug. 10, 2007

(65) Prior Publication Data

US 2008/0047328 A1    Feb. 28, 2008

Related U.S. Application Data

(63) Continuation-in-part of application No. PCT/US2006/033969, filed on Aug. 31, 2006.

(60) Provisional application No. 60/712,936, filed on Aug. 31, 2005.

(51) Int. Cl.
*G01N 11/14* (2006.01)

(52) U.S. Cl. ............................................. 73/54.28

(58) Field of Classification Search ............... 73/54.28
See application file for complete search history.

(56) References Cited

OTHER PUBLICATIONS

Tapadia, P. et al, Nonlinear Flow Behavior of Entangled Polymer Solutions: Yieldlike Entanglement Transition, Macromolecules 37, 2004, pp. 9083-9095.
Bent, J. et al, Neutron-Mapping Polymer Flow: Scattering, Flow Visualization, and Molecular Theory, Science 2003, vol. 301, pp. 1691-1695.

(Continued)

*Primary Examiner* — Hezron Williams
*Assistant Examiner* — Alex Devito
(74) *Attorney, Agent, or Firm* — Daniel J. Schlue; Roetzel & Andress

(57) ABSTRACT

The present invention relates to a rheometric device which provides a direct visualization of the subject material. The device also determines the velocity and/or the strain field across the thickness and the morphology to be determined across the same gap. The invention relates both to a device and/or method that can be used in connection with current shearing rheometers, and similar apparatus. The present invention also relates to a process for making a shear rate measurement. The invention provides versatility by allowing multiple angles of visualization which properly characterizes the flow characteristics and shear rates involved.

57 Claims, 14 Drawing Sheets

OTHER PUBLICATIONS

Macosko, C.W., Rheology: Principles, Measurements, and Applications, Wiley-VCH, New York, 1994.

Ferry, J.D., Viscoelastic Properties of Polymers, 3rd ed., Wiley, New York, 1980.

Doi, M. et al, The Theory of Polymer Dynamics, 2nd ed. (Clarendon Press, Oxford, 1988.

Hu, H. et al, Measurement of wall-slip-layer rheology in shear-thickening wormy micelle solutions, J. Rheol. 2002, 46, pp. 1001-1021.

Mooney, M. et al, The conicylindrical Viscometer, Physica 1934, 5, pp. 350-354.

Pattamaprom, C. et al, Constraint Release Effects in Monodisperse and Bidisperse Polystyrenes in Fast Transient Shearing Flows, Macromolecules 34, 2001, pp. 5229-5237.

Bercea, M. et al, Shear Rheology of Simidilute Poly(methylmethacrylate) Solutions, Macromolecules 1993, 26, pp. 7095-7096.

Menezes, E.V. et al, Nonlinear Rheological Behavior of Polymer Systems for Several Shear-Flow Histories, J. Polymer Sci.: Polymer Phys. Ed. 20, 1982, pp. 1817-1833.

Tapadia, P. et al, Yieldlike Constitutive Transition in Shear Flow of Entangled Polymeric Fluids, Phys Rev. Lett. 91, 2003, pp. 198301-1-198301-4.

Salmon, J-B. et al, Velocity Profiles in Shear-Banding Wormlike Micelles, Phys. Rev. Lett. 90, 2003, pp. 228303-1-228303-4. Chan, C-L. et al, Shear Banding in Mesoscopic Dusty Plasma Liquids, Phys. Rev. Lett. 93, 2004, pp. 220602-1-220602-4.

Kabla, A. et al, Local Stress Relaxation and Shear Banding in a Dry Foam under Shear, Phys. Rev. Lett. 90, 2003, pp. 258303-1-258303-4.

Marrucci, G., Dynamics of Entanglements: A Nonlinear Model Consistent with the Cox-Merz Rule, J. Non Newt. Fluid Mech. 62, 1996, pp. 279-289.

Graessley, W.W., The Entanglement Concept in Polymer Rheology, Adv. Polym. Sci. 16, 1974, pp. 1-179.

Smith, D.E. et al, Single-Polymer Dynamics in Steady Shear Flow, Science 283, 1999, pp. 1724-1727.

(a)

(b)

(c)

RHEOMETER ALLOWING DIRECT VISUALIZATION OF CONTINUOUS SIMPLE SHEAR IN NON-NEWTONIAN FLUID

RELATED APPLICATION DATA

This application is a continuation-in-part of co-pending International Application Number PCT/US2006/033969, with an international filing date of Aug. 31, 2006, entitled "Rheometer Allowing Direct Visualization of Continuous Simple Shear in Non-Newtonian Fluids," which published as WO2007/027850 on Mar. 8, 2007, which in turn claims priority to previously filed U.S. Provisional Application No. 60/712,936, filed on Aug. 31, 2005, entitled "Rheometer Allowing Direct Visualization of Continuous Simple Shear in Non-Newtonian Fluids", both of which are hereby incorporated by reference in their entireties.

This invention was made with government support under grants, ACS-PRF grant (40596-AC7) and NSF grant (CTS-0115867). The United States government may have certain rights to the invention or inventions herein.

FIELD OF THE INVENTION

The present invention relates to a rheometric device which provides a direct visualization of the subject material. The device also determines the velocity and/or the strain field across the thickness and the morphology to be determined across the same gap. The invention relates both to a device and/or method that can be used in connection with current shearing rheometers, and similar apparatus. The present invention also relates to a process for making a shear rate measurement. The invention provides versatility by allowing multiple angles of visualization which properly characterizes the flow characteristics and shear rates involved.

BACKGROUND OF THE INVENTION

Rheometers are used to determine the flow characteristics and visco-elastic properties of materials such as liquids, structured liquids and liquefiable materials. Rheometers typically measure material behavior such as yield stress, kinetic properties, complex viscosity, modulus, creep, and recovery. In general, rheometric measurements are made by rotating, deflecting or oscillating a measuring object in a material and measuring, for example, the torque (i.e. shear stress $\sigma$) required to do so. Typically, a rheometer comprises at least two bounding surfaces, one or more of which is moveable by rotational or other means. In a standard setup the bounding surface comprising a top flat plate, a bottom cone or vice versa and alternately a means of containing the material around a perimeter of the plate/cone.

A sample is then positioned between these surfaces, and the movable portion, typically the cone, is subject to a variable shear stress or speed. Shear rate $\dot{\gamma}$ is measured as a function of applied shear stress $\sigma$ to determine flow characteristics of the sample, one such standard measurement being viscosity. The material itself being characterized by a series of measurements at the beginning, during application of and at the end of the applied stress. At present visual representations of the material undergoing change lack clarity and depth of field.

Structured fluids such as foams, colloids, micelles, granular materials and polymers display intricate dynamic behavior that lack an adequately complete description. The flow characteristics of structured fluids can be described more accurately and/or in greater detail through direct visualization devices and related methods. However, the state of the art does not include simultaneous rheological measurements in conjunction with direct visualization and determination of the velocity field within the sample fluid. Thus, the art lacks devices and methods for direct visualization of velocity fields within rheological samples and lacks methods for visualizing the morphology of sheared samples along the velocity gradient direction.

SUMMARY OF THE INVENTION

The present invention relates to a rheometric device which provides a direct visualization of the subject material. The device also determines the velocity and/or the strain field across the thickness and the morphology to be determined across the same gap. The invention relates both to a device and/or method that can be used in connection with current shearing rheometers, and similar apparatus. The present invention also relates to a process for making a shear rate measurement. The invention provides versatility by allowing multiple angles of visualization which properly characterizes the flow characteristics and shear rates involved.

The present invention also relates to a rheometric measurement device comprising: an optically transparent fixed surface, a moving surface in a generally parallel relation to the fixed surface, the moving surface being either a flat plate, a flat surface or a conical surface having a longitudinal axis in a perpendicular relation to the fixed surface with the conical surface being in an acute angular relation to the fixed surface and the conical surface being free to rotate about its longitudinal axis, the fixed surface and moving surface being spaced apart, an optically transparent barrier occupying a perimeter about the fixed surface and the moving surface, the spacing of the fixed surface and moving surface defining an internal space bounded by the fixed surface, the moving surface and the optically transparent barrier, the internal space being able to accept material to be evaluated, the internal space being visible from outside the fixed surface, the moving surface and the optically transparent barrier, the moving surface able to move in relation to the fixed surface to create a torque on any material located in the internal space, at least one laser wherein a beam of the at least one laser impinges the moving surface and can be directed through the optically transparent surface or the optically transparent barrier, at least one visual receiving means directed to the internal space through the optically transparent surface or the optically transparent barrier and able to receive or view any material located in the internal space.

The present invention further relates to a process for conducting rheometric measurements to monitor the flow characteristics of a material, comprising the steps of: providing an optically transparent fixed mechanism having a flat first surface, providing a flat plate or a cone having a second surface with a longitudinal axis in a perpendicular relation to the first surface and the conical surface of the cone being in an acute angular relation to the first surface, wherein the second surface freely rotates about its longitudinal axis, spacing apart the first surface and the second surface, providing an optically transparent barrier occupying a perimeter around the first surface and the second surface, placing the material to monitor into the area bounded by first surface, the second surface and the optically transparent barrier and such that the material is visible, providing at least one laser, wherein a beam of the laser impinges on the second surface and is directed through the optically transparent mechanism or the optically transparent barrier, providing at least at least one visual receiving means directed at the material and able to monitor the material through the optically transparent mechanism or the optically transparent barrier, moving the second surface to create a torque on the material, and monitoring the movement of the material using the at least one visual receiving means, and the at least one laser.

The present invention further relates to a rheometric measurement device comprising: an optically non-reflective inner cylinder able to freely rotate about its longitudinal axis, an optically transparent outer cylinder encompassing the inner cylinder, the inner cylinder and outer cylinder being spaced apart to define an annular space bounded by the outer surface of the inner cylinder and the inner surface of the optically transparent outer cylinder such that the annular space is visible from outside the outer cylinder, the annular space being able to accept material to be evaluated, the inner cylinder and outer cylinder able to move in a circular motion in relation to one another and able to create a torque on any material located in the annular space, at least one laser wherein a beam of the at least one laser impinges the outer cylinder and can be directed through the optically transparent outer cylinder, at least one visual receiving means directed to the annular space and able to view any material placed into the annular space.

The present invention also relates to a process for conducting rheometric measurements to monitor the flow characteristics of a material, comprising the steps of: providing an optically non-reflective inner cylinder able to freely rotate about its longitudinal axis, providing an optically transparent outer cylinder encompassing the inner cylinder, placing the material to monitor into the annular space bounded by the outer surface of the inner cylinder and the inner surface of the outer cylinder, providing at least one laser, wherein a beam of the laser impinges the outer cylinder, providing at least one visual receiving means directed at the material and able to monitor the material through the optically transparent cylinder, rotating the inner cylinder about its longitudinal axis, and monitoring the movement of the material using the at least one visual receiving means and the at least one laser.

DETAILED DESCRIPTION OF THE INVENTION

Figure 1:
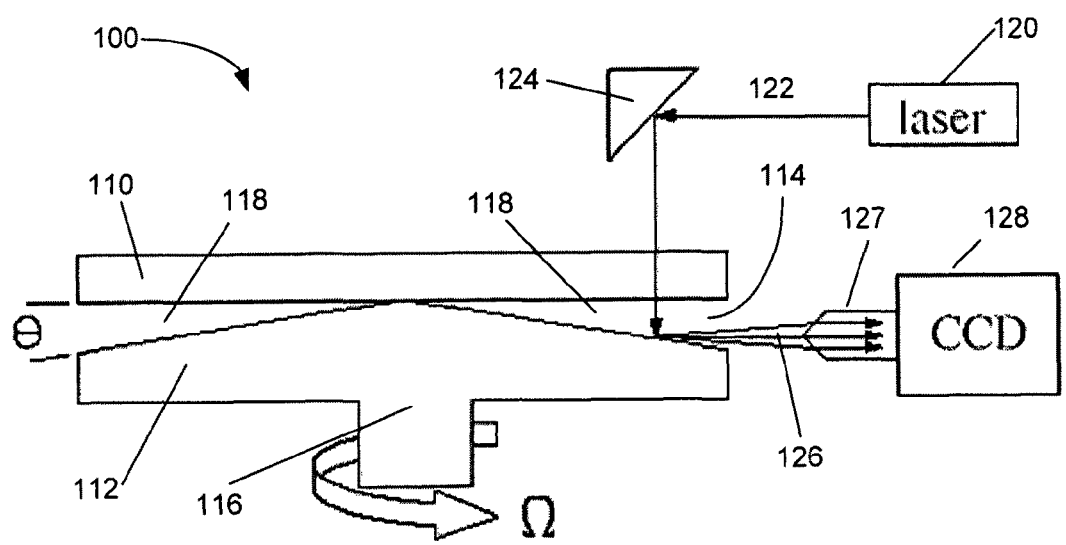
FIG. 1 is a schematic drawing of an embodiment having a sample space bounded by an upper optically transparent plate, a lower reflective plate, an optically transparent sidewall, and a laser source and detector in a 90 degree relation to each other.

The present invention relates to a rheometric device which provides a direct visualization of the subject material. The device also determines the velocity and/or the strain field across the thickness and the morphology to be determined across the same gap. The invention relates both to a device and/or method that can be used in connection with current shearing rheometers, and similar apparatus. The present invention also relates to a process for making a shear rate measurement. The invention provides versatility by allowing multiple angles of visualization which properly characterizes the flow characteristics and shear rates involved.

As used herein, the terms "one embodiment", "another embodiment", "some embodiments", and similar phrases, refers to one or more embodiments. Furthermore, the phrases may or may not refer to the same embodiment. Additionally as used herein, approximating language may be applied to modify any quantitative representation that could permissibly vary without resulting in a change in the basic function to which it is related. Accordingly, a value modified by a term such as "about" is not to be limited to the precise value specified, and can include values that differ from the specified value. Furthermore, approximating language can correspond to the precision of an instrument for measuring the value. Similarly, "free" can include an insubstantial number, or trace amounts, while still being considered free of the modified term.

In one embodiment one or more reflective particles can be disposed within a sample liquid, and tracked so as to directly visualize a velocity field within the sample. In some embodiments, the sample may be disposed within a shear cell. Appropriate shear cells include at least one optically transparent surface bounding the sample, and suitable to transmit one or more laser beams. In some embodiments the laser passes through a material and can offer a means of illuminating the material for observation. According to some embodiments, the laser beam penetrates the sample and impinges one or more of the reflective particles disposed therein. Thus, the reflective particles redirect the, i.e. reflect or scatter, at least a portion of the impinging beam. The reflected beam, or some portion thereof, then exits the sample and is transmitted through an optically transparent surface. At least a portion of the transmitted light is collected by one or more optics, and sensed by a suitable detector. According to some embodiments the detector can be operationally connected to one or more computers and/or one or more display devices. In some embodiments the computer is suitably programmed to accept data from the detector and analyze the data according to one or more suitable algorithms. The processed data can be converted to a velocity field and displayed on the display device.

In some embodiments the shear cell can include a plate and a conical surface. Either the plate or the conical surface can be stationary, while the other is capable of rotating about a central axis. Furthermore, either the plate or the conical surface can be positioned over the other regardless of which one is rotating and which is stationary. In some embodiments the space between the plate and cone is sealed and/or closed by a sidewall, thus forming a sample space. The sidewall thus retains, holds, and/or contains a liquid sample in the sample space. According to some embodiments the sidewall can be optically transparent, and in other embodiments it may be optically opaque.

According to some embodiments, samples held in the sample space can contain reflective particles suspended therein. In some embodiments a light source is used to produce a sufficiently intense beam of light, which can be directed at the sample space. The light beam is capable of reflecting and/or scattering from the suspended reflective particles, so that the reflected light can be sensed by a suitable detector. Furthermore, the light beam may be directed toward the sample space, or it can be directed by intervening optical elements toward the sample space. In any case the beam can impinge the sample space either perpendicularly, or at an oblique angle. Furthermore, the objective lens can be positioned perpendicularly or at an oblique angle relative to the impinging angle, and can direct the collected light to the detector directly or through intervening optics arranged in any appropriate geometry.

The optically transparent disk can comprise, but is not limited to, any appropriate material, including quartz, fused silica, glass, $BaF_2$, $CaF_2$, sapphire, organic polymers, or any suitable optically transparent material. Suitable materials can be completely or partially transparent, and can include neutral density filter materials, and/or band pass filter materials. Furthermore, suitable materials may or may not include imperfections of a size scale, and in sufficient quantity, to measurably alter the intensity and/or direction of at least a portion of the impinging light.

Cones can be made from, but are not limited to, any suitable material including, without limitation, ceramics, metals, alloys, glasses, suitably heat-tolerant organic compounds, or composite materials. Metals can include iron, nickel, copper, tin, aluminum, and the like, or any suitable combination or alloy thereof. Furthermore, cones can include coatings of any suitable material including, without limitation, organic coatings, precious metals, glasses, ceramics, or the like, or any combination thereof.

The side wall can comprise any of a wide variety of appropriate materials. In one embodiment, the materials are preferably optically transparent. Suitable materials can include, but are not limited to glasses, or suitably heat-tolerant polymers. Some suitable materials include, without limitation, $BaF_2$, $CaF_2$, sapphire, organic polymers, or any suitable optically transparent material. Furthermore, the sidewall can be formed, in part or as a whole, into a light-condensing lens.

Light sources can include, without limitation, lasers such as continuous wave, pulsed or Q-switched lasers, excimer lasers, diode lasers, argon lasers, YAG lasers, Nd:YAG lasers, dye lasers, gas lasers, solid state lasers, or the like. Other suitable light sources can include lamps such as white light sources, arc lamps, Xe arc lamps, Hg arc lamps, Hg(Xe) arc lamps, or any suitably intense light source. Furthermore, a suitable light source, can comprise any suitable combination of the foregoing light sources. In one embodiment, a laser used by a presenter in a lecture, provides a suitable light source means.

Detectors can include any of a wide variety of light-sensitive devices including, still cameras, video cameras, digital cameras, charge coupled devices, photodiodes, photodiode arrays, and the like. As such suitable detectors can include any appropriate optical and/or electronic elements. In one embodiment a black and white CCD camera with a sensitivity of 0.1 lux being suitable for monitoring. Alternatively, some or all optical and/or electronic elements can be separate from the detector. According to some embodiments, the detector can be free standing, or can be operably connected to a computer, which can be capable of controlling and/or collecting data from the detector. The analytical signal produced by a suitable detector can comprise an intensity reading. Alternatively, the analytical signal can be suitable to produce therefrom a still image that includes intensity data, or a moving video image that includes intensity data. The analytical signal can be collected as a function of time, and can correspond, and/or be related back to, one or more positions in the sample space. As defined a visual recording means may include any of a wide variety of light-sensitive devices including, still cameras, video cameras, digital cameras, charge coupled devices, photodiodes, photodiode arrays, a human eyeball, a visual receptor and the like. A camera may be defined as any device which detects reflected light and shows motion of the material being measured.

Suitable reflective particles can comprise metals, glasses, ceramics, organic polymers or any suitable combination thereof. Suitable metals can include, but are not limited to, precious metals such as platinum, palladium, gold, silver, or any combination thereof. Other suitable metals can include, without limitation, copper, iron, aluminum, rhenium, ruthenium, rhodium, lead, and the like, or any combination or alloy thereof. In some embodiments the reflective particles can be composites. For example, a composite can have a substantially unreflective material forming a particle core, wherein a reflective material is deposited or coated on the surface of the particle. Furthermore, the reflective particles can be added to a sample, or can comprise one or more components of the sample. In one embodiment the particles involve metallic coated glass spheres with diameters from 0.5 to 100 microns.

One embodiment is shown in FIG. 1. The apparatus 100 shown in FIG. 1 includes an optically transparent disk 110, and a cone 112 in a generally perpendicular relation with a surface of the disk 110. As shown, the cone 112 is capable of rotating about its central axis 116. The disk 110 and cone 112 can be in contact at the tip of the cone, or they can be separated by a gap. The disk and cone are bounded by an optically transparent side-wall window 114. The combination of the disk 110, the cone 112, and the window 114 form a space 118 bounded by the same. The space 118 is suitable for holding and/or containing a liquid sample having one or more reflective particles 111 disposed therein. According to this embodiment, a laser source 120 produces a laser beam 122 that is directed toward a prism 124. The prism 124 reflects the beam 122 toward the optically transparent disk 110. The disk 110 transmits the beam 122 and allows it to penetrate the sample space 118. The beam 122 impinges one or more reflective particles 111 disposed within the sample space 118, and is scattered therefrom. Thus, a portion of scattered light 126 exits the side wall window 114 and is collected by an objective lens 127 and sensed by a detector 128. In this embodiment the rotating surface is the uppermost surface, however in other embodiments the rotating surface can be the lowermost surface.

In one embodiment, a method according to the present invention includes using direct visualization of a sample flow field as part of making a rheometric measurement. Some embodiments enable measuring a velocity field in real time during controlled-rate shear or controlled-stress shear. According to some embodiments, a velocity field within a sample can change significantly over time. In some embodiments this may occur during a period at or near the start of applying a controlled-rate shear, which may coincide with a stress plateau.

One embodiment includes tracking the velocity of one or more particles disposed in the sample. According to some embodiments the velocity field of an entangled polymer solution in simple shear ($\dot{\gamma}$) can be non-linear. According to one embodiment, there can be a discontinuous relationship between $\sigma$ and $\dot{\gamma}$. The velocity gradient can be non-uniform and the velocity field can change, i.e. evolve, over time in response to a controlled-rate startup shear in the stress plateau region. It is recognized by one of skill in the art that stress plateau regions are commonly encountered in entangled polymers.

According to some embodiments a velocity field in a sample evolves with time. In some embodiments the field can be linear at the start of shear. In some embodiments the field can attain a maximum deviation from linearity in a transient state. The transient state can precede a steady state that is characterized by a velocity gradient varying explicitly along the sample thickness.

One embodiment can include evaluating polymers and/or any other viscoelastic materials including emissions, gels, suspension, and multi-component fluids. In some embodiments such an evaluation can enable higher quality and/or stronger polymer products, and can lower production costs, by enabling the practitioner to adjust process parameters accordingly.

The method and apparatus of the present invention is applicable to any rheometer or shearing device involving a need for flow visualization of the velocity profile in real time during both controlled-rate and controlled-stress shear. The present invention can also be used to provide a visual input or can be used in combination with a prior art rheometer to provide a viscosity measurement.

A cone-plate shear cell is one such device used to explore the constitutive behavior of structured liquids including entangled polymers as it allows a the production of a continuous simple shear. This device generates uniform simple shear flow for both Newtonian and non-Newtonian liquids, provided that their constitutive relations are invertible. Regarding polymeric liquids as simple fluids, researchers routinely shear their samples in a cone-plate flow cell by imposing an angular velocity $\Omega$ on one of the two surfaces as shown in FIG. 1. A constitutive relation is determined by measuring the corresponding torque required to maintain $\Omega$, assuming that a uniform shear rate $\dot{\gamma}=\Omega/\theta$ would be created across the sample thickness. This mode of imposing a constant surface velocity has become a standard protocol known as controlled-rate shear and was thought to generate a linear velocity profile in the gap independent of the constitutive behavior.

Monodisperse entangled polymer solutions were found to display a flow transition under a constantly applied shear stress at a certain stress level, where the resulting apparent shear rate could be orders of magnitude higher than its value below $\sigma_c$. The controlled-rate measurements only turned up a smooth continuous flow curve with a characteristic stress plateau. Thus, depending on which variable (surface velocity vs. applied force) is controlled in generating the simple shear, there exist two different flow curves for the same sample.

Rheometrical measurements are typically made/performed at room temperature, however these measurements can vary based upon the experimentation required. Factors which alter the testing environment include, but are not limited to, the materials used, the potential reaction of the materials involved, the need to study at a higher or lower temperate or any other factor which warrants temperature deviations. These changes/needs will require the sample to be encased in a hotter or colder, in some cases extreme hot or cold, environments. Such environments can alter the sample temperatures to between about −100° C. and 200° C. To achieve these setups typically an oven or refrigeration apparatus is utilized around the unit. Such a setup requires that the laser and camera devices have access to the appropriate means of visual monitoring. (i.e. the heating/cooling units must allow access to the clear plate and/or the clear barrier at the perimeter of the plate.

FIG. 1 shows a schematic of the setup of the particle tracking velocimetry, where the upper stationary plate is made of transparent glass, the lower rotating cone made of steel and $\theta=5°$. The apparatus allows for a view of the velocity field at a specific radial position in the gap, and affords good spatial and time resolutions. The device of FIG. 1 can be used as an accessory to a commercial rheometer, allowing in-situ observations in conjunction with rheological information.

In one embodiment. the entangled polymer solution evaluated is a 10 weight percent 1,4-polybutadiene (PBD) solution, made of a high weight PBD of $M_w=1.24\times10^6$ g/mol and $M_w/M_n=1.2$ from (Polymer Source Inc. P1445-Bd) dissolved in a phenyl-terminated oligomeric butadiene of $M_n=1.0$ K (Aldrich 200417). For particle tracking purposes, the sample is seeded with silver-coated particles of 10 micron diameter (Dantec Dynamics HGS-10) at a low level of ca. 200 ppm. A controlled-rate shear rheometer (ARES) equipped with a cone-plate assembly of 25 mm diameter is employed to take velocity profile measurements. The cone angle θ of the device is 5°.

The particle tracking velocimetry of the present invention comprises sending a laser beam along the velocity gradient direction through the gap between cone and plate and video-taping the illuminated moving particles over time with a CCD (charge coupled device) camera facing the gap as shown in FIG. 1. A thin film surrounds the meniscus to allow focus of a tele-microlens onto the interior illuminated particles. One concern found negligible involves the confining film on the simple shear flow inside the cone-plate. This lack of influence this has been estimated and experimentally verified. In one embodiment the moving surface is optically non-reflective.

In one embodiment, the camera used is a standard camera. In another embodiment the camera is a CCD camera. In another embodiment the camera contains a normal lens apparatus. In another embodiment the camera employs an objective lens apparatus. The camera devices vary based upon the application and needs and are not limited by any one embodiment listed herein. Any means of visually receiving images are possible.

Figure 2A:
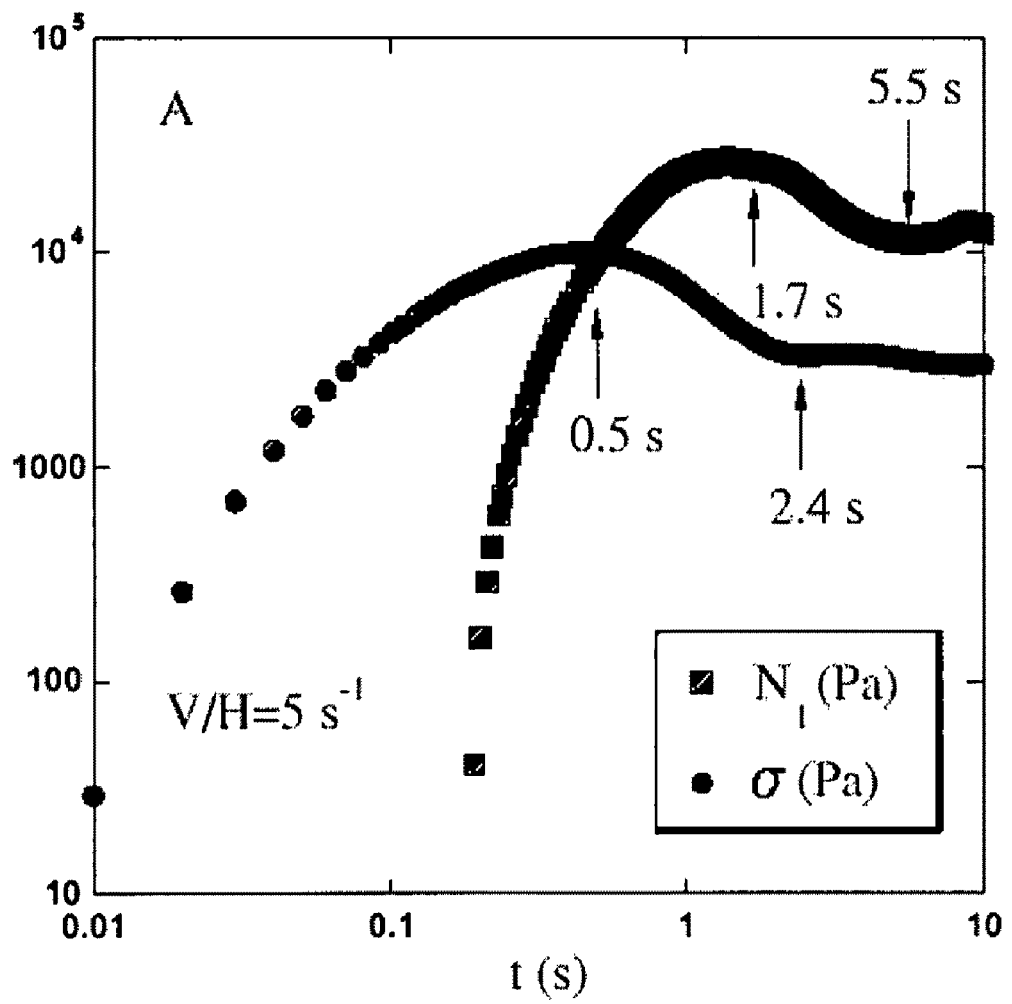
FIG. 2(A) is a set of plots showing growth upon startup shear at shear rate 5 s$^{-1}$ of both shear and normal stresses ($\sigma$ and $N_1$ respectively) as measured using an embodiment of the present invention.

The flow fields in the cone-plate cell were examined at three imposed shear rates of 0.05, 0.1 and 5 s$^{-1}$. These rates respectively correspond to the Newtonian region, the region just before the stress plateau, and the region well inside the stress plateau. At the two low values of $\dot{\gamma}=\Omega/\theta$, i.e., two low values of angular velocity $\Omega$, the stresses grow monotonically. However at 5 s$^{-1}$, FIG. 2A shows non-monotonic behavior in both shear (σ) and normal ($N_1$) stresses, where a σ first grew to its maximum at t=0.5 and then dropped to its steady state value at t=2.4 s, meanwhile the first normal stress $N_1$ reached its maximum at t=1.7 s and approached its steady state around t=5.5 s. The feature of overshoots (especially of σ) is a known for entangled polymers under high shear. Such overshoots have been understood to be the flow characteristic of a uniformly sheared sample.

Figure 2B:
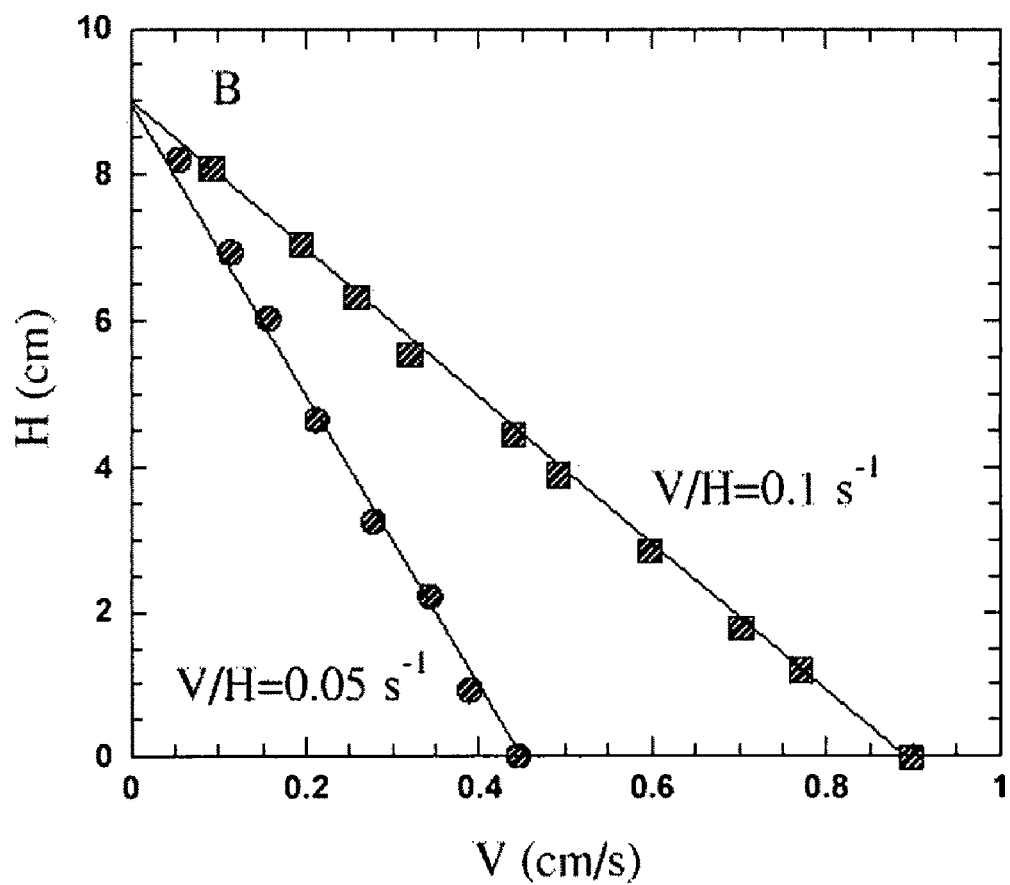
FIG. 2(B) is a set of plots showing velocity profiles of a well-entangled 10% PBD solution at shear rates of about 0.05 and 0.1 s$^{-1}$ at any time, where the straight lines indicate linear profiles as measured using an embodiment of the present invention.
Figure 2C:
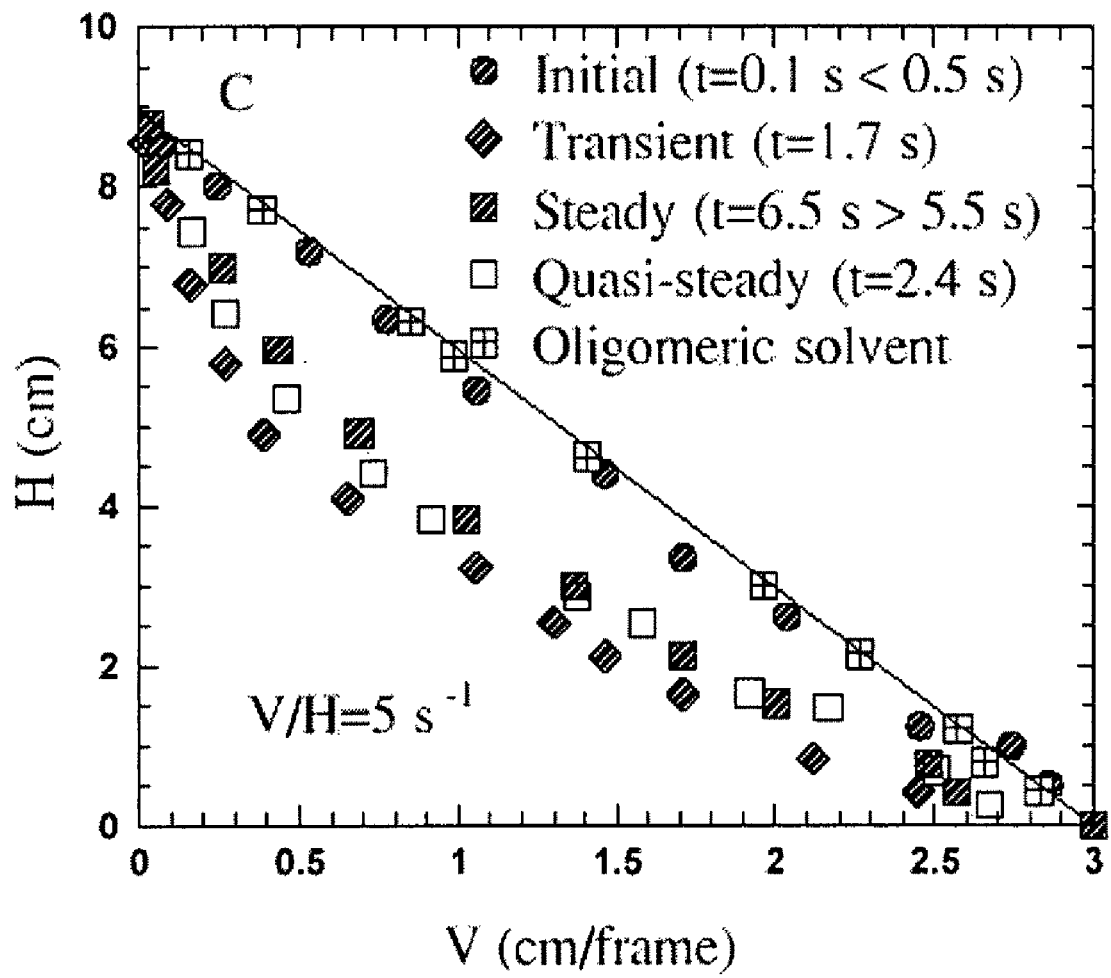
FIG. 2(C) is a set of plots showing the velocity profiles of several fluids at shear rates of about 5 s$^{-1}$, at initial (circles), transient (diamonds), quasi-steady state (open squares) and steady state (squares), as measured with an embodiment of the present invention having a video monitor.

As shown in FIG. 2B, particle track velocimetric (PTV) measurements demonstrate velocity gradients are essentially uniform along the gap at the low shear rates. At a higher shear rate of 5 s$^{-1}$, i.e., when the angular velocity of the rotating cone is set to $\Omega=5\theta=0.44$ rad/s, the velocity field no longer varies linearly across the gap as shown in FIG. 2C. In contrast, when a Newtonian oligomeric butadiene liquid (which was used as the solvent for the 10% PBD solution) is subjected to the same shearing condition at 5 s$^{-1}$, a constant value equal to the preset value prevails at all times in every layer in the gap, as shown by the plus-filled squares in FIG. 2C. The gap distance H shown in FIGS. 2B and 2C was ca. 0.9 mm (i.e., about 10 mm from the cone center) this distance correlates to 9 cm on the video monitor where the experimental measurements were taken.

This first set of particle tracking velocimetric observations reveals the entangled polymeric liquid in a state of frustration when subjected to an average shear rate that falls in the window of flow discontinuity, from a shear rate of 0.2 to 40 s$^{-1}$. In other words, the entangled chains prefer to be sheared at 0.2 s$^{-1}$ and lower or 40 s$^{-1}$ and higher. When the imposed angular velocity $\Omega$ is such that $\Omega/\theta=5$ s$^{-1}$, falling in the middle of this window, the system satisfied this boundary condition by sampling a spectrum of shear rates. The local shear rate at the top stationary plate was smaller than 1/6 of the prescribed value of 5 s$^{-1}$, whereas the local shear rate at the rotating cone doubles from 5 to 10 s$^{-1}$.

This velocity profile evolved over time. Corresponding to the characteristic times indicated in FIG. 2A, one can show that the velocity gradient is initially constant across the gap up to the point of the stress maximum, i.e., up to t=0.5 s. The maximum deviation from this linear velocity profile occurred around the maximum of $N_1$, or at t=1.7 s. The eventual steady state possessed a weaker nonlinear profile, as shown in FIG. 2C, which was not reached until after $N_1$ had stabilized at 5.5 s. In other words, the profile was still evolving at t=2.4 s when the shear stress σ had already stabilized.

Apart from these explicit rheological and PTV measurements in FIG. 2, the process of the present invention provides a direct visual impression of the variations of the velocity profile across the gap with time.

Figure 3:
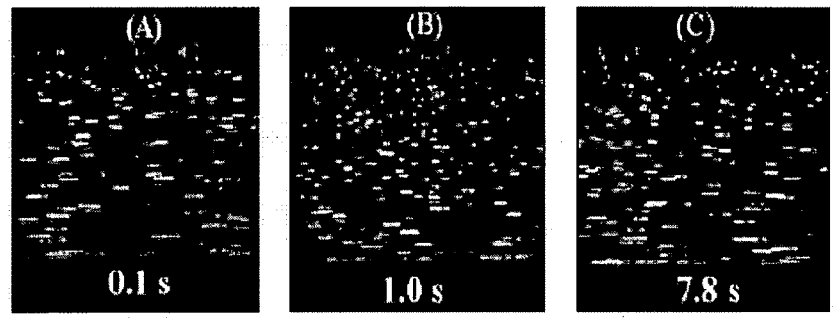
FIG. 3 is a set of three still pictures captured from a video recording of reflective particles that are illuminated and moving within a sample at (A) initial (t=0.1), (B) transient (t=1.0 s) and (C) steady (t=7.8 s) states at apparent shear rate of $\Omega/\theta=10$ s$^{-1}$, where the distance between the two horizontal lines, H, is about 0.9 millimeter, and the moving surface is optically non-reflective.

FIG. 3 details three photos taken from the gap of the particle movements for a shear rate of $\Omega/\theta=10$ s$^{-1}$ at three characteristic times corresponding to initial, transient and steady states. The exposure time of the CCD camera is $\Delta t=1/60$ s. The still pictures from the video recording detail the illuminated moving particles at (A) initial (t=0.1), (B) transient (t=1.0 s) and (C) steady (t=7.8 s) states for an imposed apparent shear rate of $\Omega/\theta=10$ s$^{-1}$, where the distance between the two horizontal lines, H, is 0.9 mm. In this embodiment, only the particles in focus yield the brightest spots and streaks. From the length $\Delta x$ of the streak generated by the moving light-scattering particle, one can compute the speed of the particle according to $V=\Delta x/\Delta t$. Thus, the streak length is directly proportional to the particle speed V since $\Delta t$ is fixed during the video recording. The three pictures clearly show different streak length variations along the gap, indicating different velocity profiles similar to those measured in FIG. 2 for 5 s$^{-1}$ at the different times. When analyzing in real time the particle motion at a lower shear rate of $\Omega/\theta=2.5$ s$^{-1}$ is easier to decipher.

The particle tracking velocimetric method of the present invention provides flow responses of entangled polymer, solutions in a commonly employed shear device of cone-plate, examines the controlled-rate shear measurements that assume a uniform velocity gradient in space and examines the long-standing research tradition in the area of non-Newtonian flow of complex materials.

Liquids that possess a linear relationship between shear stress σ and shear rate $\dot{\gamma}$ are known as Newtonian fluids, with a proportionality constant of viscosity η. Polymeric liquids, made of long linear chains that form entanglements, since they cannot pass over one another without breaking, are/an important class of non-Newtonian fluids. Such liquids have a viscosity η which requires a finite time to reach a steady state value and decreases with $\dot{\gamma}$. This shear thinning behavior was thought to occur gradually due to increased chain alignment in shear that leads to disentanglement. If the chain disentanglement event was not to occur catastrophically in shear flow as currently known in the art, shear thinning would take place homogeneously in every layer across the sample thickness. Then, just as in the case of Newtonian fluids, imposition of V on one surface over the other stationary surface in a parallel-plate device of gap H would indeed result in a homogeneous flow with shear rate V=H prevailing in every layer.

Structured materials such as micellar solutions, dense suspensions, foams, liquid crystals, soft gels and glasses, granular fluids, or metals respond to large external deformation catastrophically. That is, the imposed shear deformation or rate of deformation produces a spatially nonhomogeneous distribution of different states across the sample thickness. This phenomena is commonly known as shear banding. Entangled model polymer solutions have shown a spatial variation in the shear rate measured across the sample thickness in startup shear. This finding makes it rather difficult to establish a constitutive relationship between σ and $\dot{\gamma}$ through rheological measurements. This also challenges the version of the theoretical description of entangled polymers in shear flow that arose from efforts based on the de Gennes' visualization of snakelike motion of a test chain within the Edwards' tube picture. Furthermore, this requires an reexamination of previous experimental studies of similar entangled polymer solutions.

The previous results on continuous shear behavior of entangled polymer solutions have led to further experiments in the present invention regarding how chains actually negotiate with each another in establishing new topological relationships during shear. Specifically, in this work, we apply large-amplitude oscillatory shear (LAOS) to illustrate intriguing flow behaviors of entangled liquids by using an effective particle-tracking velocimetric method to determine the velocity profile in LAOS. The results indicate that chain disentanglement, the cause of shear thinning, also occurs inhomogeneously in space in LAOS.

The entangled polymer solutions under examination are a previously prepared and studied 10 wt. % 1,4-polybutadiene (PBD) solution, made of a high weight PBD of $M_w$=1:2×10$^6$ g=mol and $M_w/M_n$=1:18 from Polymer Source, Inc., dissolved in a phenyl-terminated oligomeric butadiene (oBD) of $M_n$=1:0 kg/mol (Aldrich 20041-7), and a newly made 10% PBD solution of a monodisperse PBD of $M_w$=740 kg/mol (prepared by Bridgestone) in a monodisperse oBD of Mw=4 kg/mol (prepared by Goodyear). For particle-tracking purposes, the sample was seeded with silver-coated particles of 10 μm diameter (Dantec Dynamics HGS-10) at a level of several hundred parts per million. A strain-controlled shear rheometer equipped with a cone-plate assembly of 25 mm diameter was employed.

Figure 4:
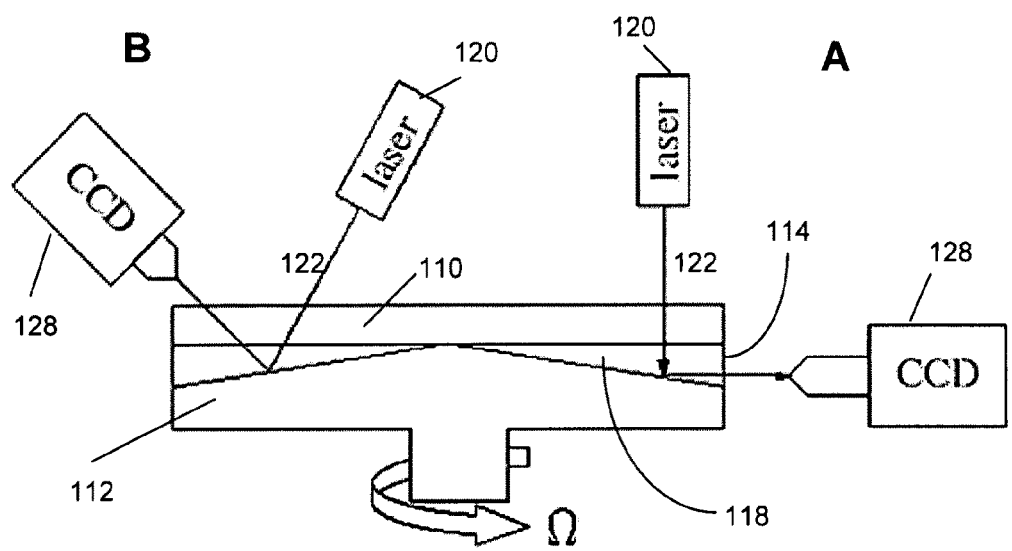
FIG. 4(A) is a schematic drawing one embodiment comprising a laser impinging a surface of the apparatus at about 90 degrees and detecting scattered light at about 90 degrees relative to the laser source.
FIG. 4(B) is a schematic drawing of another embodiment comprising a laser impinging a surface of the apparatus at an oblique angle and detecting scattered light at about 90 degrees relative to the laser source.

The particle-tracking velocimetry, illustrated in FIG. 4, details two separate embodiments possible for the laser 120 and camera 128. As shown these two embodiments involve directing a laser beam 122 along the velocity gradient direction or at an angle to the shearing surface and videotaping the illuminated moving particles with a black-white CCD camera (with minimum 0.3 lx and maximum 30 frames per second) mounted with a DIN objective (3:2 x) through an adaptive tube (Edmund Optics: U54-868). As stated previous, two setups are possible based on the setup of the rheometric machine. In scheme A, a transparent film 114 surrounds the meniscus to allow focus of a telemicrolens onto the interior 118. The perturbation of the confining film on the simple shear flow inside the cone-plate cell can be evaluated and is removable by employing scheme B. In the present work, scheme A was set up for an advanced rheometrics expansion system, where a bottom cone rotates against a fixed upper plate; scheme B was set up for a Bohlin CVOR rheometer (Malvern Instruments) where an upper cone rotates. The invention is not limited by either apparatus, with the scheme chosen based on the ultimate properties desired from the instrument.

Oscillatory shear occurs by sandwiching a sample between cone 112 and plate 110, as shown in FIG. 4, where the cone 112 makes an oscillatory torsional motion against the fixed plate 110, as described by angular displacement $\phi(t)=\phi_0 \sin(\omega t)$ and velocity by $\Omega=\phi_0\omega \cos(\omega t)$. The shear strain is taken to be uniform across the gap equal to $\gamma_0=X_0(r)/h(r)\approx\phi_0/\theta$, with $X_0(r)=\phi_0 r_o$, where $h(r)=r \tan \theta \approx r\theta$ is the gap distance at r. At low amplitudes $\gamma_0 \ll 1$, the storage modulus G' and loss modulus G" are a function of $\omega$, indicating that the overall chain relaxation rate, i.e., the crossover frequency $\omega_c$ (at which G'=G"), is approximately 0.07 rad/s for the entangled liquid. When the oscillatory shear is applied at frequencies $\omega > \omega_c$, the entangled chains deform and orient affinity without relaxing significantly during the shear reversal in each cycle.

The sample was subjected to LAOS for a relatively long time frame at $\omega$=1 rad/s>$\omega_c$ to illustrate the effect of LAOS on molecular reorganization. In the first cycle, the shear deformation was uniform across the gap, and such a uniform deformation prevailed for $\gamma_0 \leq 1$ even at longer time frames. However, over time unexpected results occurred. One key result of the particle-tracking velocimetric measurements is detailed in FIG. 5. As a way to visualize the effect of LAOS, the velocity field at the instant of the maximum $\Omega$ of the rotating cone was analyzed. The video recording was also analyzed at additional moments during each cycle. The measurements involve playing the movie frame by frame at a fixed rate of 30 frames per second using MGI VIDEOWAVE 4 software for about one to three frames and measuring, on a computer monitor, the displacement of the traced particles over these frames in the different layers across the sample thickness. The time resolution being approximately 0.1 s. In contrast to the linear velocity profile seen for $\gamma_0$=1 and at the beginning for $\gamma_o$=4, the steady state velocity profiles are highly nonlinear. The actual gap distance H was ca. 0.9 mm (i.e., about 10 mm from the cone center) and was 12 cm on the video display, where the measurements were taken and presented in FIG. 5. The user can access a movie showing the evolution of the velocity profile for $\gamma_0$=3, based on the open and solid squares obtained in FIG. 5.

To remove potential complications introduced by the confining film around the meniscus, we examined the velocity profile at LAOS of a separate 10% PBD solution using a second rheometer from Malvern Instruments where an upper cone rotates against a fixed lower plate. Using scheme B depicted in FIG. 4, the set of velocity profiles shown in FIG. 6 were obtained. The banding behavior being similar to that shown in FIG. 5, and the differences arising from the difference in the makeup of these two different samples. Thus, this result indicates a negligible effect at the location of observation from the stationary film surrounding the meniscus in scheme A in FIG. 4. To rule out the possibility that the observed banding would be due to a tiny stress gradient in the cone-plate setup, similar experiments have been conducted using parallel-disk shear cells, and the foregoing banding systematically observed.

Figure 5:
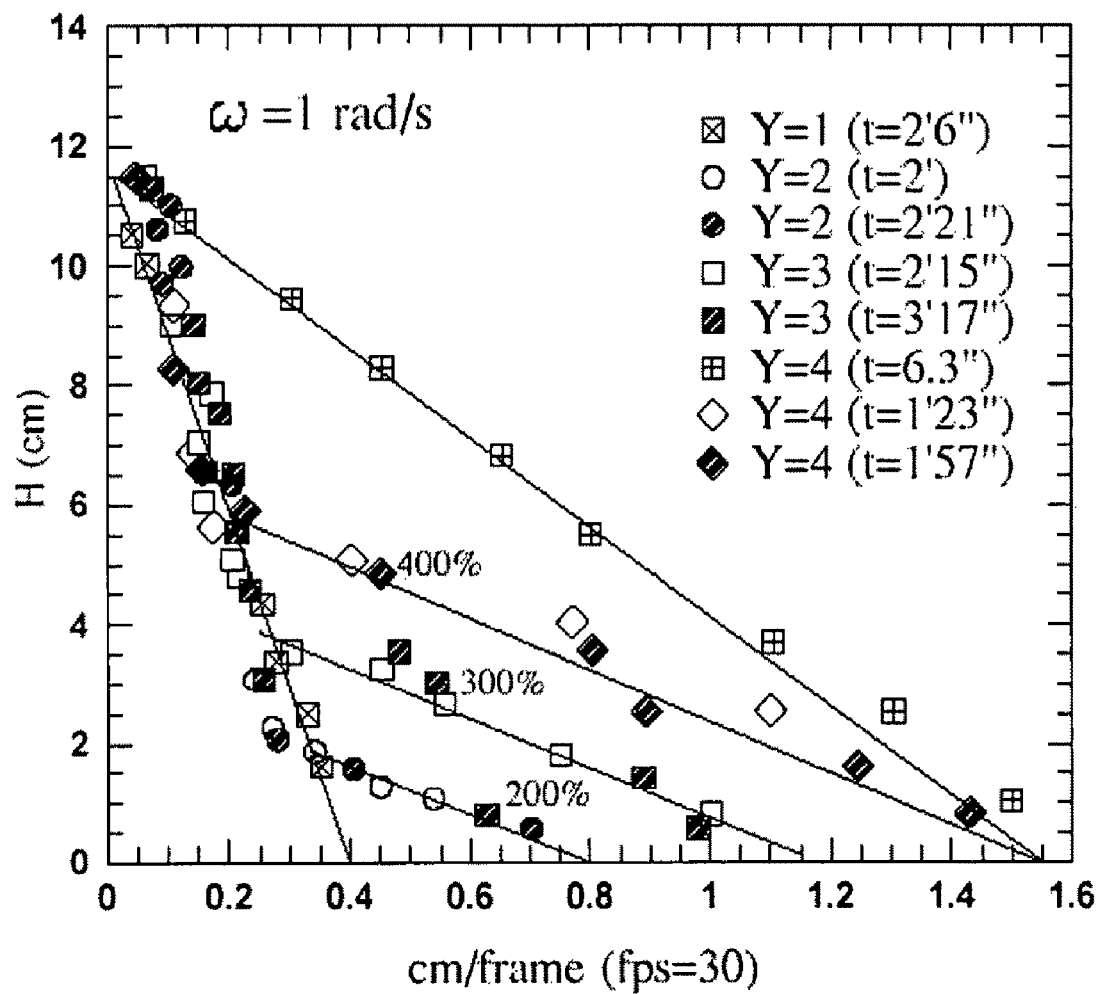
FIG. 5 is a set of plots showing velocity profiles in large amplitude oscillatory shear of various samples as measured according to an embodiment of the present invention.

Returning to FIG. 5, we note the banding characteristics to depend on the amplitude of the imposed strain. The peak shear rate $\gamma'_0=\omega\gamma_0$ in the "fluid" layer reached 7:2 s$^{-1}$, whereas the "solid" top layer experienced a peak shear rate nearly tenfold smaller. In other words, the bottom layer experienced a shear strain as high as over 700%, whereas the top layer remained intact and was only undergoing deformation no greater than 100%. Upon increasing $\gamma_0$ from 2 to 4, the fractional thickness f of the fluid layer increased from ⅙ to ½, which can be described by f=($\gamma_0$−1)/6, implying that no part of the sample would transform to a "fluid," i.e., f=0 when $\gamma_0 \leq 1$, which is indeed the case as shown in FIG. 5.

To elucidate the dynamics of this phenomenon, one follows the evolution (i.e., the thickness growth) of the disentangled layer over time. The flow behavior of the fluid-like layer is different from that of the solid-like layer as is shown on the visual impression of the recorded video. Using the video, one watches the bottom layer growing in time and stopping the video play to determine its thickness at the resulting time intervals. The first step involves looking for amplitude effect at a fixed oscillation frequency of $\omega$=1 rad=s. FIG. 4(*a*) details that the sample reached its final state during the same time interval (ca. 100 s) regardless of the value of $\gamma_0 > 1$.

Figure 7A:
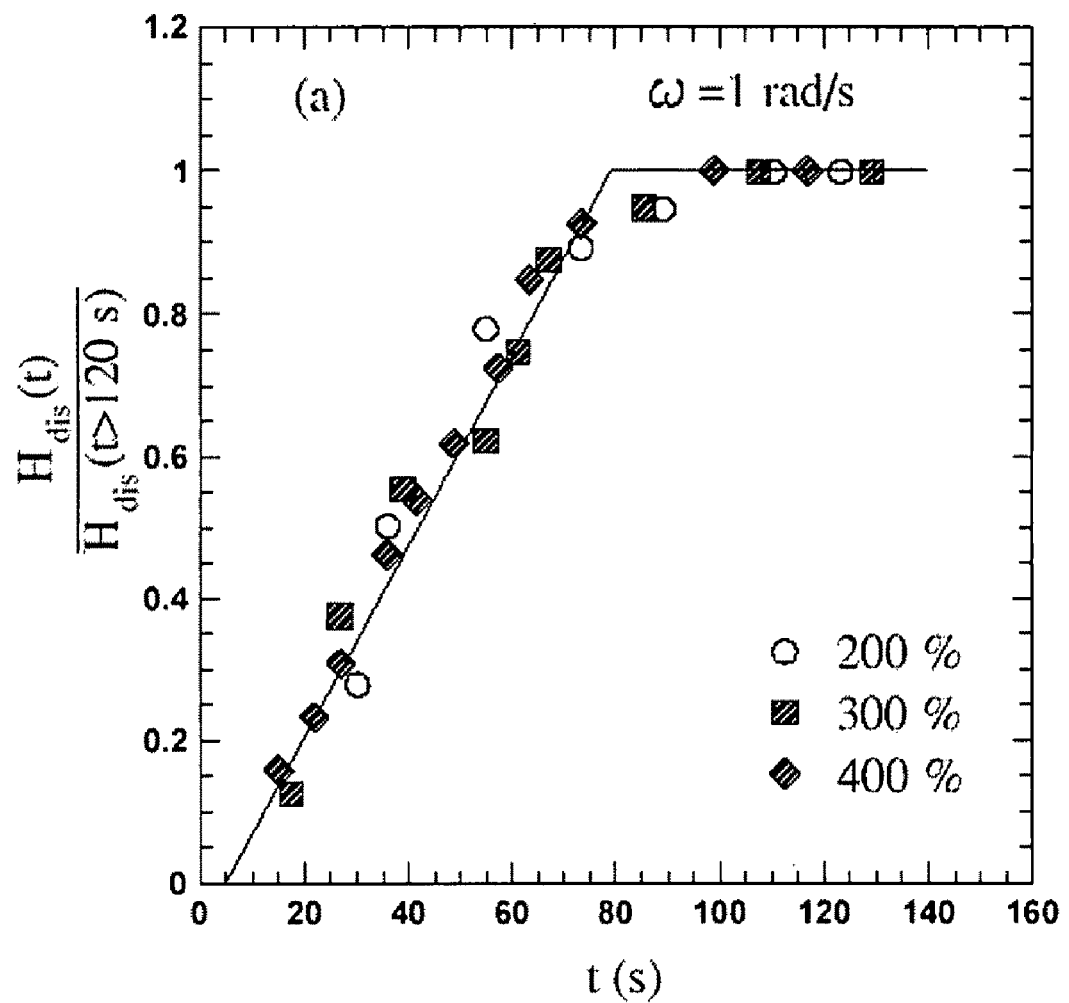
FIG. 7(A) is a plot showing the effect of varying oscillation frequency while keeping the amplitude constant and above the chain relaxation rate of 0.07 rad/s.
Figure 7B:
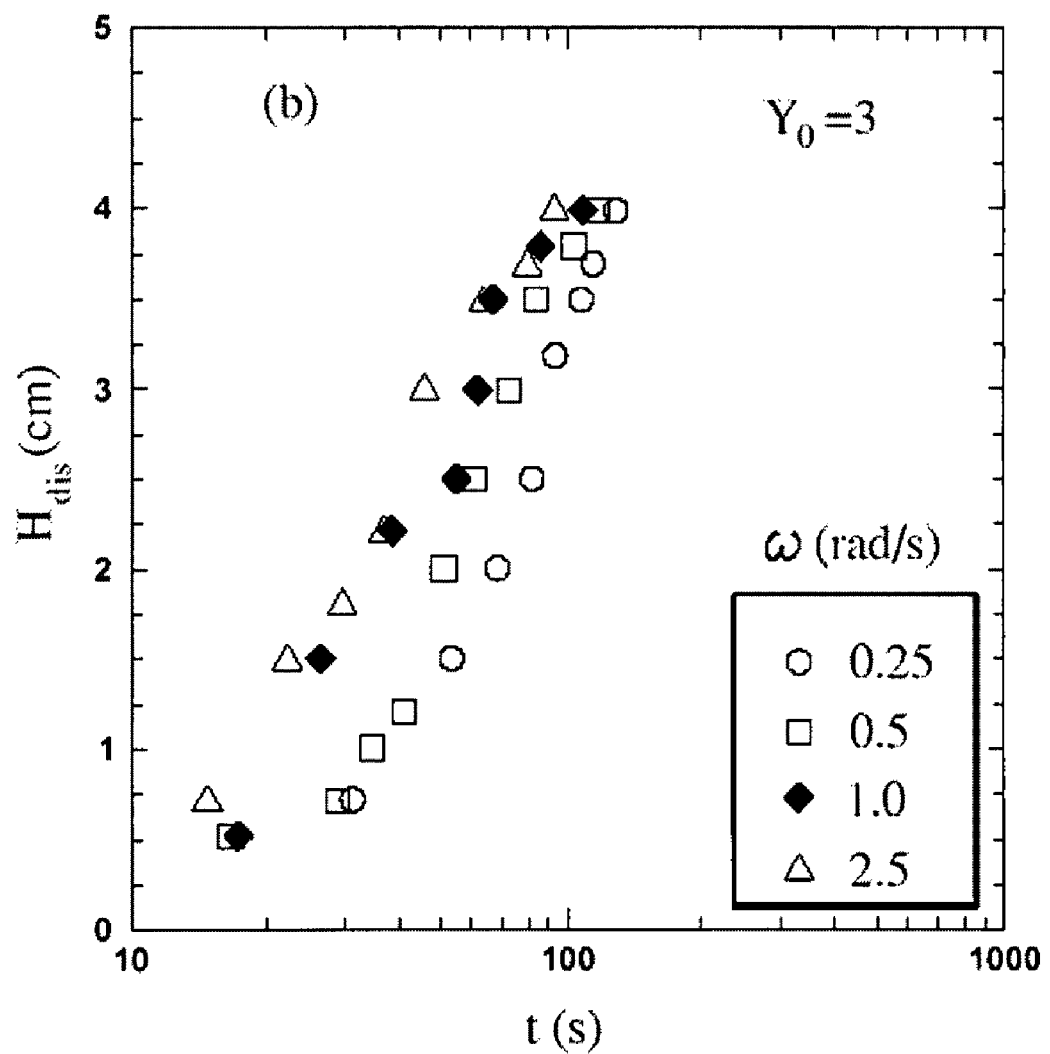
FIG. 7(B) is a set of plots showing the effect of varying oscillation frequency while keeping the amplitude constant above the chain relaxation rate of 0.07 rad/s.

The next step subjected the sample to an amplitude of $\gamma_0$=3 at various oscillation frequencies higher than the chain relaxation rate of $\omega_c=0.07$ rad/s. Independent of the oscillation frequency, the final thicknesses of the fluid layer attained 4 cm on the video monitor, or ca. ⅓ of the total sample thickness, at approximately the same time, that is, around 100 s as shown in FIG. 7B. Since ω differed by a factor of 10, in a given duration the sample had been subjected to 10 times the cycles at ω=25 rad/s as it had at ω=0.25 rad/s. Conversely, the total amount of cumulative shear strain $\gamma_t$ was 10 times smaller at 0.25 than at 2.5 rad/s. FIG. 7B details the growth time hardly being dependent on $\gamma_t$ and ω and depended only on the time the sample was subjected to the LAOS at $\omega > \omega_c$, indicating that flow convection played a minor role. FIG. 7A further indicates as long as the strain amplitude is high enough (i.e., $\gamma_0 > 1$) to produce sufficient chain orientation, the kinetics leading to the final state are essentially the same, independent of $\gamma_0$. This behavior is true for the present highly polydisperse sample. Monodisperse samples display a different set of phenomena.

The preceding experimental observations indicate that the entangled solution rearranges over time into different states of entanglement in the various layers of simple shear. Specifically, the LAOS produced over time a coexistence of two different states of chain entanglement, indicating that the sample could not undergo chain disentanglement and shear thinning uniformly across the sample thickness. The key controlling variable appears to be a sufficiently high level of chain orientation as determined by the amplitude of the oscillatory shear. As long as the oscillation frequency is higher than the chain relaxation rate allowing the imposed LAOS to produce long-lasting chain orientation, the initially well-entangled chains find themselves in a new, anisotropic environment allowing them to find a different topological relationship. With sufficient chain orientation, the chains seem to clear of each other's way and enter a new dynamic state of less mutual constraint in a spatially inhomogeneous fashion, with some layers absorbing the imposed strain by transforming into a state of disentanglement, and allowing the rest of the sample to stay in a nearly equilibrium state of entanglement. The resulting movie details the entanglement actually took roughly one period or a few seconds for the fluid layer to become visible, whereas the time required for the transformed layer to grow to its final thickness is much longer. The kinetics governing the growth is insensitive to both ω and $\gamma_0$. At present, there lacks a theoretical description available to account for the nucleation and growth of the disentangled state in shear oscillation. In the near future the available theoretical framework should provide an adequate description of this reported phenomena.

Figure 6:
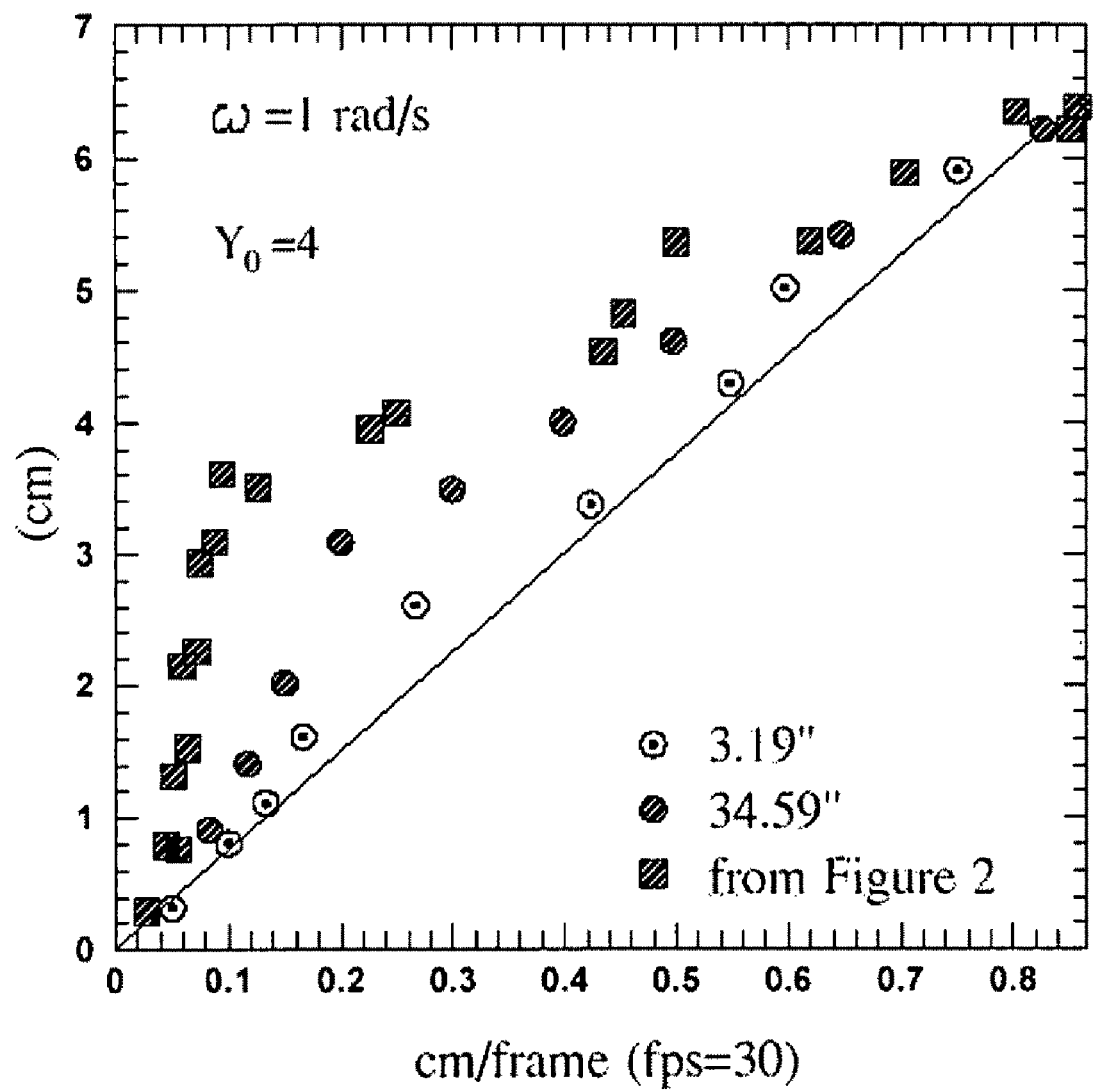
FIG. 6 is a plot of data showing the banding behavior as observed using the scheme detailed in FIG. 4B.

The entangled polymer solution was found to respond to strain-controlled large-amplitude oscillatory shear by transforming partially into a state of lower viscosity and, thus, a lower level of chain entanglement. The response shows a state of frustration because the transformation (i.e., chain disentanglement) could not take place homogeneously as shown in FIGS. 5 and 6. The coexistence of two layers of different viscoelastic properties under a given LAOS details that chain disentanglement nucleates unevenly in space, taking place only under the critical condition of sufficient chain orientation. Here the "nucleation" occurs through chain diffusion evidenced by the observations in FIGS. 7A and 7B. Current experimentation details other banding features not observed here exist for the polydisperse solutions.

Figure 8A:
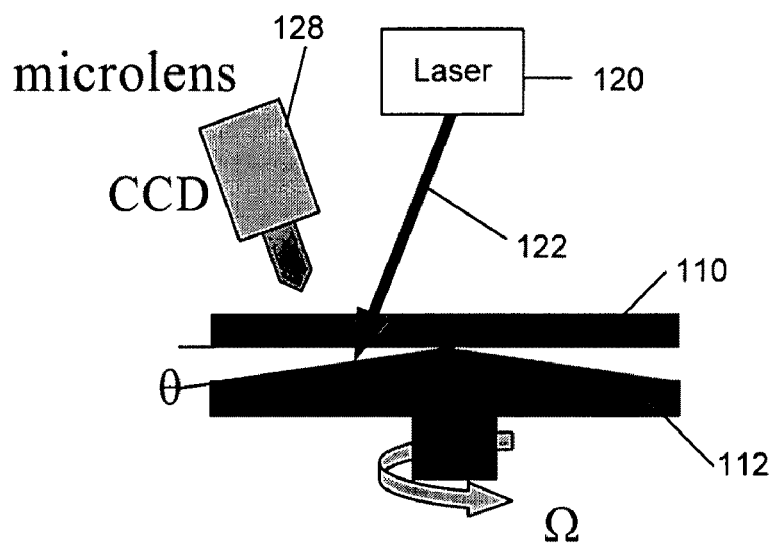
FIG. 8(A) is a drawing showing an embodiment comprising a laser and CCD detector at an oblique angle relative to each other and relative to the surface of a shear cell.

The present invention is not limited to a setup where the camera is positioned perpendicular to the longitudinal axis of the cone and the laser perpendicular to the stationary plate. As mentioned previous, additional embodiments of the camera and laser setup are possible. As detailed in FIG. 8, the camera 128 and laser 120 setup can vary based on the application, instrumentation and/or material being used and/or evaluated. As shown in FIG. 8A the camera 128 and laser 120 operate by measuring through the top clear plate 110, both devices being located so as to view the rheological material and the resulting tracing devices through the plate. The laser 120 is located either perpendicular to the clear plate 110 or at an angle so as to create a means for the CCD camera 128 to observe through the same plate. The CCD camera 128 is then positioned at a perpendicular to the plate or at an angle to the plate so as to be able to monitor the material via the laser and the methods described previous. Various angles and setups in this manner are possible with the only limitation being the ability of the camera to read the laser. In order to accomplish this various changes are possible to the angle of the cone 112, the angle or position of the prism 124, the position of the laser 120, and the position of the camera 128.

Figure 8B:
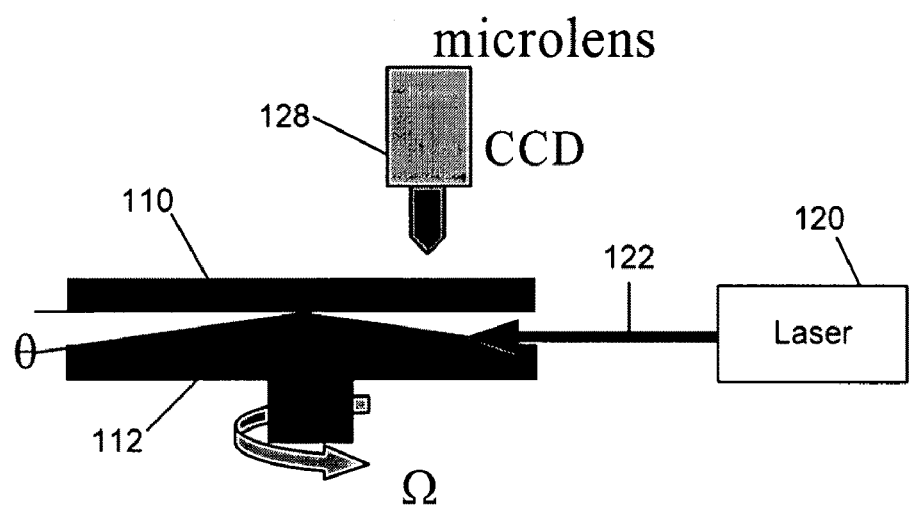
FIG. 8(B) is a drawing showing an embodiment comprising a laser and CCD detector oriented at about ninety degrees relative to each other and relative to a shear cell.

Another embodiment of the setup, as shown in FIG. 8B involves the camera 128 monitoring via the top clear plate 110. The camera 128 is setup either perpendicular to the plate or at an angle so as to be able to monitor the laser 120. The laser 120 is setup in a plane perpendicular to the longitudinal axis or at an acute angle to this axis. The laser 120 is directed into the material and the tracing material through the optically clear barrier occupying the perimeter of the plate and cone. FIG. 8B differs from FIG. 1 in that the laser penetrates the sample from the side in FIG. 8B and penetrates the sample from the top through the clear plate in FIG. 1.

Figure 9:
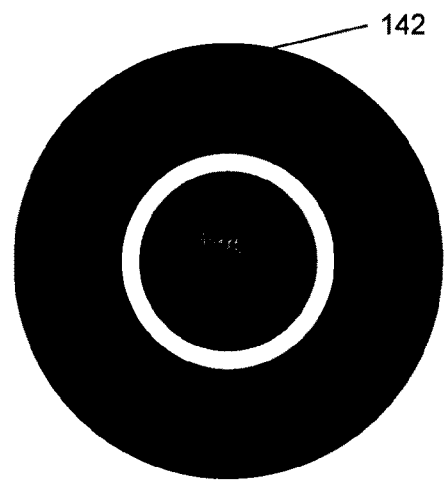
FIG. 9 is a drawing of one embodiment of the setup showing the Pollett design of a cone-plate shear cell which avoids any effect coming from edge fracture on the rheological measurements, where the fixed upper surface is made of a circular disk that is connected to a force transducer and a ring that is held in place without touching the disk and is supported to rest directly on the bottom base, (1) top view, (b) side view and (c) as shown from the angled-viewpoint.
Figure 9:
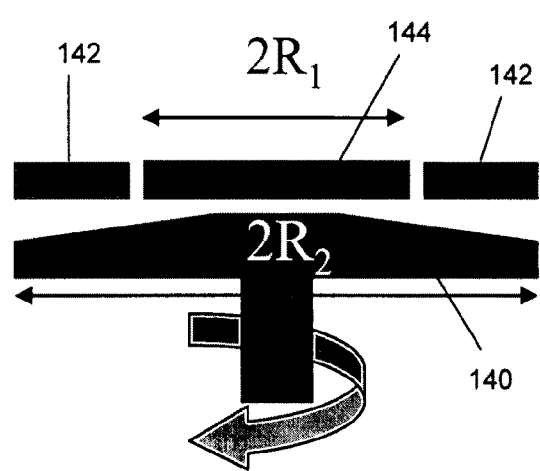
Figure 9:
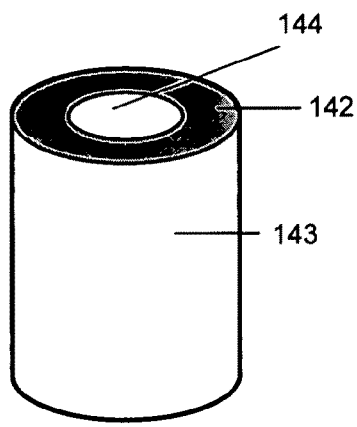

Another embodiment involves an alteration to the design of the cone-plate assembly itself. FIG. 9 details a modified setup known as a Pollet design, with a cone 140 and other supporting apparatus. FIG. 9 details the Pollett design of a cone-partitioned plate shear cell. Such a setup avoids any effect coming from edge fracture on the Theological measurements, where the fixed upper surface is made of a circular disk 144 that is connected to a force transducer, a ring 142 and in some instances a support 143 that is held in place without touching the disk 144 and is fixed to the bottom of the instrument as shown in FIG. 9.

Figure 10:
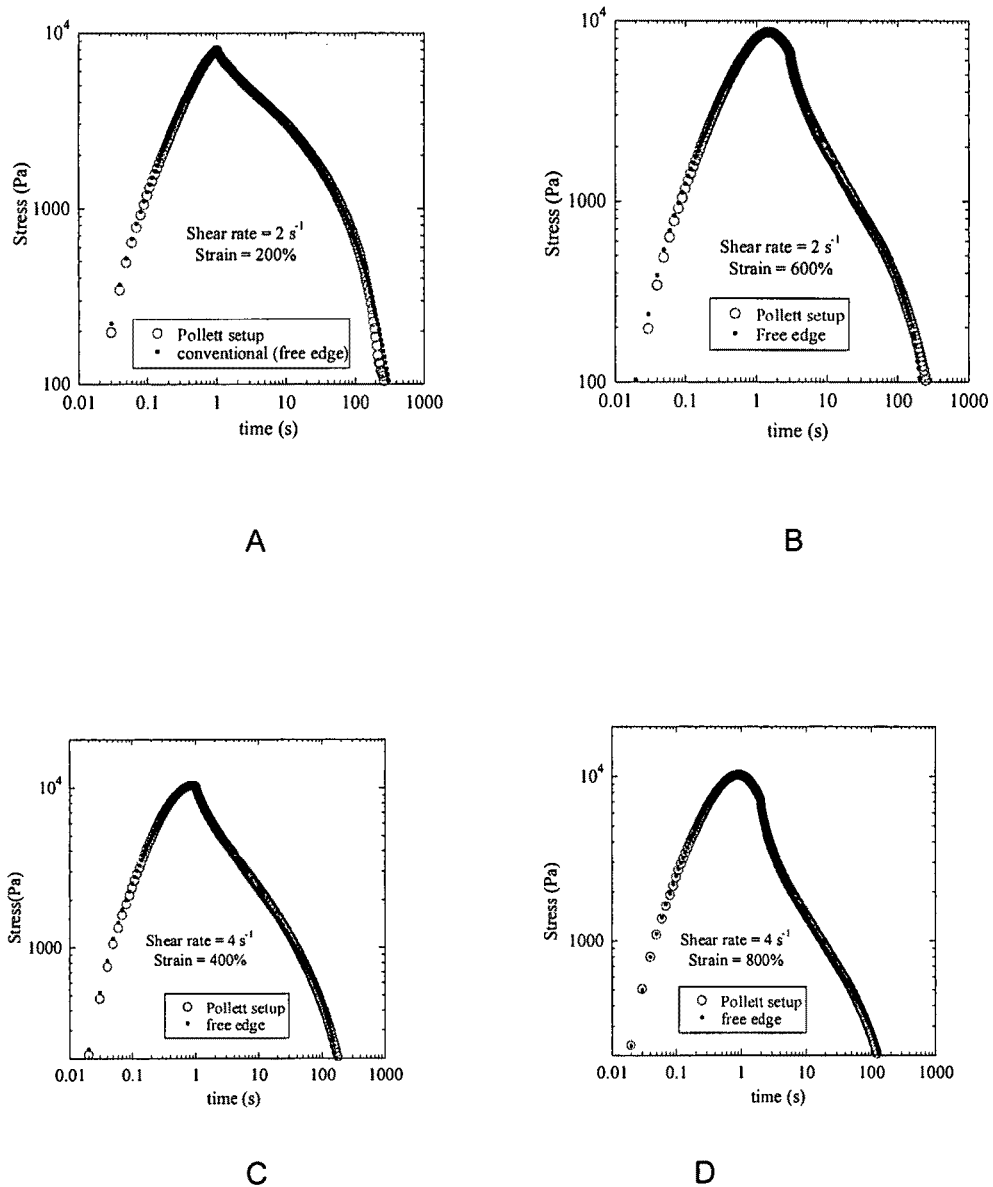
FIG. 10 are a set of measurements of the shear and normal stress made using the setup of FIG. 9 to show the perfect match between conventional and new design of FIG. 9 for cases where edge fracture is absent. In other words, one sample involves a size of $2R_2$ where the measurement only picks up contributions from $\pi(2R_1)^2$ area, and in the other experiment, the sample merely extends to an area of $\pi(2R_1)^2$, the four figures compared the stress relaxation under four conditions, where $R_2=20$ mm and $R_1=12.5$ mm.
Figure 11:
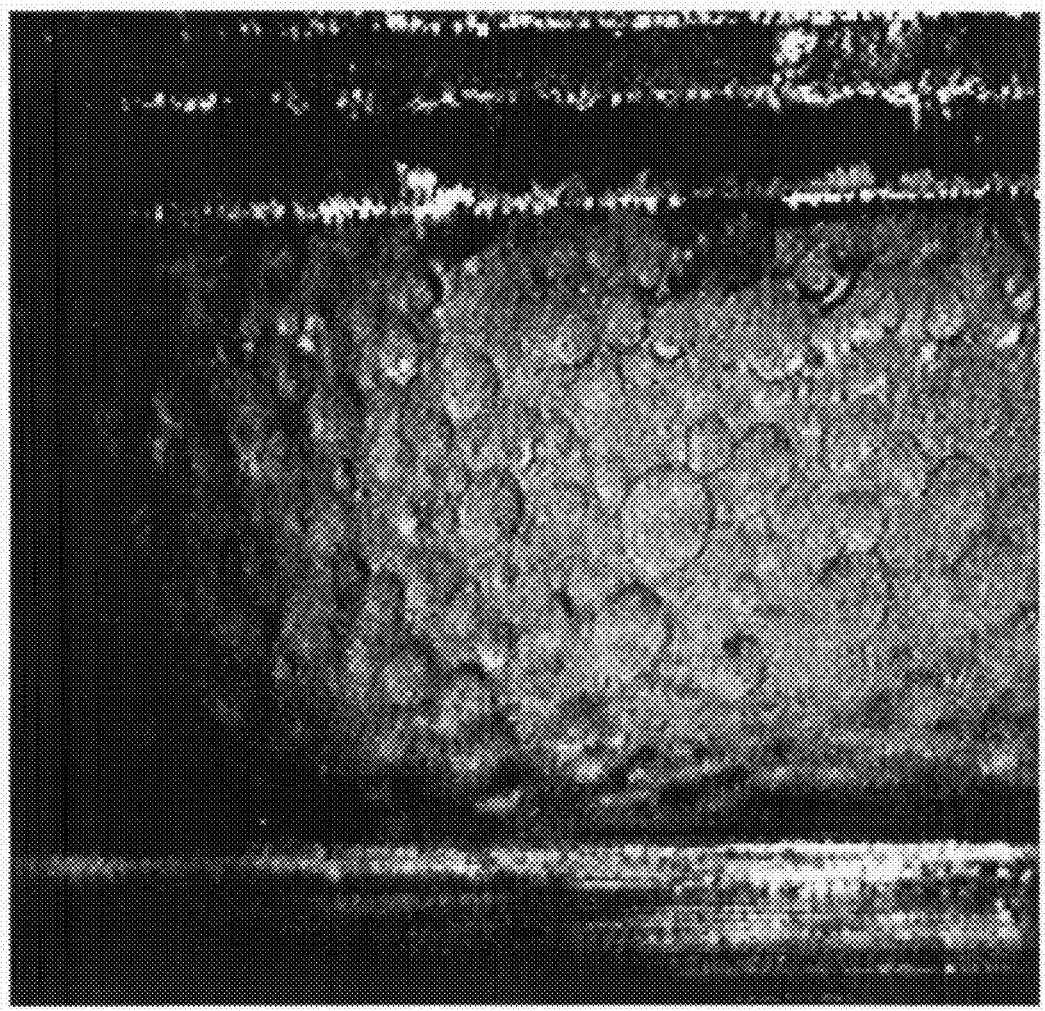
FIG. 11 is a still-image from the setup shown in FIG. 4 which details a model immiscible blend under shear, the still image coming from a movie.

The setup of a Pollet design from FIG. 9 is detailed in FIG. 10 via the graphs of the data obtained versus a standard setup. In these comparison two sets of graphs measurements of the shear and normal stress relaxations were made both with and without the "black" ring 142 to protect the edge. In other words, one sample involves a size of $2R_2$ where the measurement only picks up contributions from $\pi(2R_1)^2$ area, and in the other experiment, the sample merely extends to an area of $\pi(2R_1)^2$, the four figures compared the stress relaxation under four conditions, where $R_2=20$ mm and $R_1=12.5$ mm. See FIGS. 10(a) thru 10(d).

Figure 12:
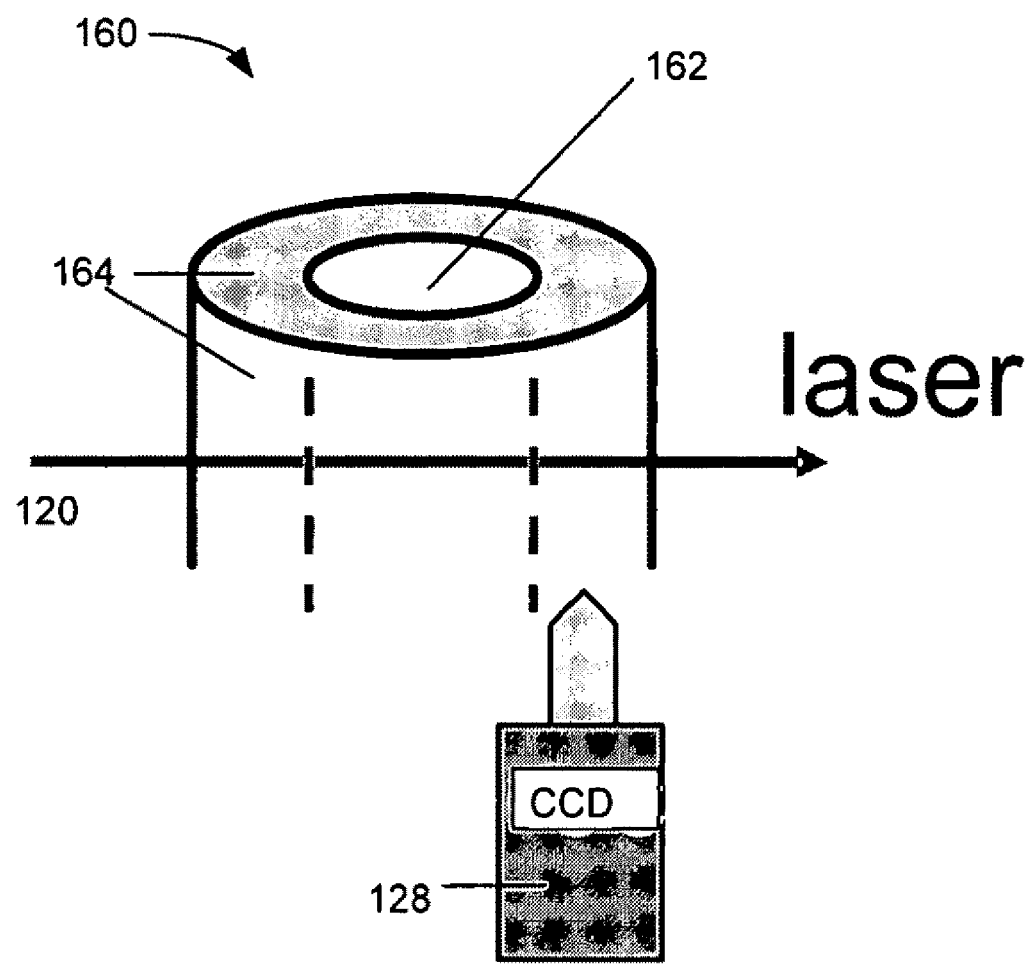
FIG. 12 is a schematic drawing of an embodiment known as a Couette design, the drawing detailing the optically transparent outer cylinder and the non-reflective rotating inner cylinder with a horizontally traveling laser incident into the co-cylinder and a camera located at the bottom of the Couette cell.

Another embodiment shown in FIG. 12 is known in the art as a Couette design. A Couette type apparatus 160 employs two cylinders, an inner cylinder 162 and an outer cylinder 164. In this embodiment the outer cylinder 164 is optically transparent. Such transparency allows light sources such as a laser 120 to penetrate the walls of the instrument and allows a camera 128 or recording means the ability to ascertain the properties of the material in between the two cylinders. The inner cylinder 162 typically being non-reflective. A laser 120 or other light source typically travels horizontal to the co-cylinders 162, 164. A camera 128 or other recording means operates at the bottom of the Couette cell and allows the material between the cylinders to be monitored.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A rheometric measurement device comprising:
   an optically transparent fixed surface;
   a moving surface in a generally parallel relation to the fixed surface, the moving surface being either a flat plate, a flat surface or a conical surface having a longitudinal axis in a perpendicular relation to the fixed surface with the conical surface being in an acute angular relation to the fixed surface and the conical surface being free to rotate about its longitudinal axis, and wherein the fixed surface and moving surface are spaced apart;
   an optically transparent barrier occupying a perimeter about the fixed surface and the moving surface, wherein the spacing of the fixed surface and moving surface define an internal space bounded by the fixed surface, the moving surface and the optically transparent barrier, wherein the internal space is able to accept material to be evaluated, wherein the internal space is visible from outside the fixed surface, the moving surface and the optically transparent barrier, and wherein the moving surface is able to move in relation to the fixed surface in order to create a torque on any material located in the internal space;
   at least one laser wherein a beam of the at least one laser impinges the moving surface and can be directed through the optically transparent surface or the optically transparent barrier; and
   at least one visual receiving means directed to the internal space through the optically transparent surface or the optically transparent barrier and able to receive or view any material located in the internal space.

2. The device of claim 1, further comprising at least one display means connected to the at least one visual receiving means to monitor the torque placed on any material within the internal space.

3. The device of claim 1, further comprising at least one recording means connected to the at least one visual receiving means to monitor the torque placed on any material within the internal space.

4. The device of claim 3, wherein the at least one recording means records at a rate of at least about 30 frames per second.

5. The device of claim 1, wherein the laser is directed through the optically transparent surface at an angle from substantially parallel to the transparent surface to perpendicular to the transparent surface.

6. The device of claim 1, wherein the laser is directed through the optically transparent barrier at an angle from substantially perpendicular to the optically transparent barrier to substantially parallel to the transparent barrier.

7. The device of claim 1, wherein the at least one visual receiving means is directed at an angle from substantially parallel to the transparent surface to perpendicular to the transparent surface.

8. The device of claim 1, wherein the at least one visual receiving means is directed at an angle from substantially perpendicular to the optically transparent barrier to substantially parallel to the transparent barrier.

9. The device of claim 1, wherein one or more tracing means partially occupies the internal space.

10. The device of claim 9, wherein the one or more tracing means are one or more silver coated particles.

11. The device of claim 9, wherein the one or more tracing means have a diameter between about 1 micron and about 100 microns.

12. The device of claim 9, wherein the one or more tracing means are combined with the material being evaluated and the concentration of tracing means in the material is between about 10 and about 1000 parts per million.

13. The device of claim 1, wherein the torque created is via a circular oscillation.

14. The device of claim 1, wherein the torque creates a shear rate of between about $0.2s^{-1}$ and about $40s^{-1}$.

15. The device of claim 1, wherein the flat surface and conical surface setup further comprises a Pollet design with the transparent surface having an outer ring around an inner plate.

16. The device of claim 15, wherein the laser is directed through the optically transparent surface at an angle from substantially parallel to the transparent surface to perpendicular to the transparent surface and the at least one visual receiving means is directed at an angle from substantially perpendicular to the optically transparent barrier to substantially parallel to the transparent barrier.

17. A process for conducting rheometric measurements to monitor the flow characteristics of a material, comprising the steps of:
   providing an optically transparent fixed mechanism having a flat first surface;
   providing a flat plate or a cone having a second surface with a longitudinal axis in a perpendicular relation to the first surface and the conical surface of the cone being in an acute angular relation to the first surface, wherein the second surface freely rotates about its longitudinal axis;
   spacing apart the first surface and the second surface;
   providing an optically transparent barrier occupying a perimeter around the first surface and the second surface;
   placing the material to monitor into the area bounded by first surface, the second surface and the optically transparent barrier and such that the material is visible;
   providing at least one laser, wherein a beam of the laser impinges on the second surface and is directed through the optically transparent mechanism or the optically transparent barrier;
   providing at least at least one visual receiving means directed at the material and able to monitor the material through the optically transparent mechanism or the optically transparent barrier;
   moving the second surface to create a torque on the material; and
   monitoring the movement of the material using the at least one visual receiving means, and the at least one laser.

18. The process of claim 17, wherein at least one display means is connected to the at least one visual receiving means.

19. The process of claim 17, wherein at least one recording means is connected to the at least one visual receiving means.

20. The process of claim 19, wherein the at least one visual recording means monitors and records at a rate of at least about 30 frames per second.

21. The process of claim 17, wherein monitoring the movement includes collecting data from the resultant movement of the material and recording the data.

22. The process of claim 21, wherein the data is converted to velocity as a function of time.

23. The process of claim 17, wherein the laser is directed through the optically transparent fixed mechanism at an angle from substantially parallel to the first surface to perpendicular to the first surface.

24. The process of claim 17, wherein the laser is directed through the optically transparent barrier at an angle from substantially perpendicular to the optically transparent barrier to substantially parallel to the transparent barrier.

25. The process of claim 17, wherein the at least one visual receiving means is directed through the optically transparent fixed mechanism at an angle from substantially parallel to the first surface to perpendicular to the first surface.

26. The process of claim 17, wherein the at least one visual receiving means is directed through the optically transparent barrier at an angle from substantially perpendicular to the optically transparent barrier to substantially parallel to the transparent barrier.

27. The process of claim 17, wherein one or more tracing means are suspended in the material.

28. The process of claim 27, wherein the one or more tracing means are silver coated particles.

29. The process of claim 27, wherein the one or more tracing means have a diameter of between about 1 micron and about 100 microns.

30. The process of claim 27, wherein the concentration of the one or more tracing means in the material is between about 10 and about 1000 parts per million.

31. The process of claim 17, wherein the shear rate between the first surface and the second surface is between about $0.2s^{-1}$ and about $40s^{-1}$.

32. The process of claim 17, wherein the movement of the second surface is via a circular oscillation.

33. The process of claim 17, wherein the monitoring of the movement of material includes collecting as a function of time video images of the positions of various reference points in the material.

34. The process of claim 17, wherein the monitoring of the movement of material includes converting the images obtained to a velocity versus vertical position plot.

35. The process of claim 17, wherein the flat plate and cone having a second surface setup further comprises a Pollet design with the optically transparent fixed mechanism having an outer ring around an inner plate.

36. A rheometric measurement device comprising:
an optically non-reflective inner cylinder able to freely rotate about its longitudinal axis;
an optically transparent outer cylinder encompassing the inner cylinder, wherein the inner cylinder and outer cylinder are spaced apart to define an annular space bounded by the outer surface of the inner cylinder and the inner surface of the optically transparent outer cylinder such that the annular space is visible from outside the outer cylinder, wherein the annular space is able to accept material to be evaluated, and wherein the inner cylinder and outer cylinder is able to move in a circular motion in relation to one another and able to create a torque on any material located in the annular space;
at least one laser wherein a beam of the at least one laser impinges the outer cylinder and can be directed through the optically transparent outer cylinder; and
at least one visual receiving means directed to the annular space and able to view any material placed into the annular space.

37. The device of claim 36, further comprising at least one display means connected to the at least one visual receiving means to monitor the material within the annular space.

38. The device of claim 36, further comprising at least one recording means connected to the at least one visual receiving means to monitor the material within the annular space.

39. The device of claim 38, wherein the at least one visual recording means records at a rate of at least about 30 frames per second.

40. The device of claim 36, wherein one or more tracing means partially occupies the annular space.

41. The device of claim 40, wherein the one or more tracing means are one or more silver coated particles.

42. The device of claim 40, wherein the one or more tracing means have a diameter between about 1 micron and about 100 microns.

43. The device of claim 40, wherein the one or more tracing means are combined with the material being measured and the concentration of tracing means in the material is between about 10 and about 1000 parts per million.

44. The device of claim 36, wherein the torque creates a shear rate of between about $0.2s^{-1}$ and about $40s^{-1}$.

45. A process for conducting rheometric measurements to monitor the flow characteristics of a material, comprising the steps of:
providing an optically non-reflective inner cylinder able to freely rotate about its longitudinal axis;
providing an optically transparent outer cylinder encompassing the inner cylinder;
placing the material to monitor into the annular space bounded by the outer surface of the inner cylinder and the inner surface of the outer cylinder;
providing at least one laser, wherein a beam of the laser impinges the outer cylinder;
providing at least one visual receiving means directed at the material and able to monitor the material through the optically transparent cylinder;
rotating the inner cylinder about its longitudinal axis; and
monitoring the movement of the material using the at least one visual receiving means and the at least one laser.

46. The process of claim 45, wherein at least one display means is connected to the at least one visual receiving means.

47. The process of claim 45, wherein at least one recording means is connected to the at least one visual receiving means.

48. The process of claim 47, wherein the at least one visual recording means monitors and records at a rate of at least about 30 frames per second.

49. The process of claim 45, wherein monitoring the movement includes collecting data from the resultant movement of the material and recording the data.

50. The process of claim 49, wherein the data is converted to velocity as a function of time.

51. The process of claim 45, wherein one or more tracing means are suspended in the material.

52. The process of claim 51, wherein the one or more tracing means are silver coated particles.

53. The process of claim 51, wherein the one or more tracing means have a diameter of between about 1 micron and 100 microns.

54. The process of claim 51, wherein the concentration of the one or more tracing means in the material is between about 10 and about 1000 parts per million.

55. The process of claim 45, wherein rotating the inner cylinder creates a shear rate between the cylinders of between about $0.2s^{-1}$ and about $40s^{-1}$.

56. The process of claim 45, wherein the monitoring of the movement of material includes collecting as a function of time video images of the positions of various reference points in the material.

57. The process of claim 45, wherein the monitoring of the movement of material includes converting the images obtained to a velocity versus vertical position plot.

* * * * *